United States Patent
Loxley et al.

(10) Patent No.: US 9,872,829 B2
(45) Date of Patent: *Jan. 23, 2018

(54) CORE SHEATH DRUG DELIVERY DEVICES

(71) Applicant: Chemo Research, S.L., Madrid (ES)

(72) Inventors: Andrew Loxley, Philadelphia, PA (US); Mark Mitchnick, East Hampton, NY (US); Gonzalo Hernández Herrero, Madrid (ES); Celestino Ronchi, Milan (IT)

(73) Assignee: Chemo Research, S.L., Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 14/855,187

(22) Filed: Sep. 15, 2015

(65) Prior Publication Data

US 2016/0000706 A1    Jan. 7, 2016

Related U.S. Application Data

(63) Continuation of application No. 13/766,592, filed on Feb. 13, 2013, now Pat. No. 9,132,081.

(60) Provisional application No. 61/598,642, filed on Feb. 14, 2012.

(51) Int. Cl.
| | |
|---|---|
| *A61K 31/567* | (2006.01) |
| *A61K 31/569* | (2006.01) |
| *A61K 31/57* | (2006.01) |
| *A61K 45/06* | (2006.01) |
| *A61K 47/32* | (2006.01) |
| *A61K 47/34* | (2017.01) |
| *A61K 9/00* | (2006.01) |
| *A61F 6/14* | (2006.01) |

(52) U.S. Cl.
CPC ............ *A61K 9/0036* (2013.01); *A61F 6/142* (2013.01); *A61K 9/0002* (2013.01); *A61K 9/0092* (2013.01); *A61K 31/567* (2013.01); *A61K 31/569* (2013.01); *A61K 31/57* (2013.01); *A61K 45/06* (2013.01); *A61K 47/32* (2013.01); *A61K 47/34* (2013.01)

(58) Field of Classification Search
CPC .............. A61K 2300/00; A61K 31/567; A61K 31/569; A61K 31/57; A61K 45/06; A61K 47/32; A61K 47/34; A61K 9/0002; A61K 9/0036; A61K 9/0092; A61F 6/142
See application file for complete search history.

(56) References Cited

U.S. PATENT DOCUMENTS

| 5,972,372 A | 10/1999 | Saleh et al. | |
|---|---|---|---|
| 2010/0034863 A1* | 2/2010 | Fairhurst | A61K 9/5063 424/423 |
| 2010/0040671 A1 | 2/2010 | Ahmed et al. | |
| 2010/0166826 A1* | 7/2010 | Kiser | A61F 6/08 424/426 |

FOREIGN PATENT DOCUMENTS

| EP | 1732520 B1 | 12/2006 |
|---|---|---|
| WO | WO2008061963 A2 | 5/2008 |
| WO | WO2009094573 A2 | 7/2009 |
| WO | WO2011116132 A1 | 9/2011 |

OTHER PUBLICATIONS

J.A.H. van Laarhoven, et al., In Vitro Release Properties of Etonogestrel and Ethinyl Estradiol from a Contraceptive Vaginal Ring, ("the year of publication is sufficiently earlier than the effective U.S. filing date and any foreign priority date so that the particular month of publication is not an issue"), 2002, pp. 163 173, vol. 232, Elsevier, International Journal of Pharmaceutics,Amsterdam,NL.

T. Higuchi, Mechanism of Sustained Action Medication, Theoretical Analysis of Rate of Release of Solid drugs Dispersed in Solid Matrices, Dec. 1963, pp. 1145 1149, vol. 52, Wiley, Journal of Pharmaceutical Sciences, Hoboken NJ US.

International Search Report of the International Searching Authority. International Application No. PCT/EP2013/052855 issued by the European Patent Office, dated Sep. 9, 2013, Rijswijk, Netherlands.

PCT International Preliminary Report on Patentability,Application No. PCT/EP2013/052855, International Filing Date Feb. 13, 2013, Date of Mailing of IPRP May 7, 2014, 16 pages, issued by the International Preliminary Examining Authority, European Patent Office, Rijswijk, Netherlands.

* cited by examiner

*Primary Examiner* — Snigdha Maewall
(74) *Attorney, Agent, or Firm* — Peter B. Scull; Hamilton DeSanctis & Cha, LLP

(57) ABSTRACT

It relates to a device comprising (a) a core comprising polyurethane; (b) a sheath comprising ethylene vinyl acetate copolymer, said sheath substantially or completely surrounding said core; and (c) one or more active pharmaceutical ingredients dissolved or dispersed in said core and/or said sheath; and to a process for its preparation.

24 Claims, 4 Drawing Sheets

CORE SHEATH DRUG DELIVERY DEVICES

This application claims the benefit of the U.S. Provisional Patent Application Ser. No. 61/598,642 filed on Feb. 14, 2012.

FIELD OF THE INVENTION

The present invention relates to core sheath drug delivery devices with a core of polyurethane substantially or completely surrounded by a sheath of ethylene vinyl acetate copolymer. The core and/or sheath of the device further contain one or more active pharmaceutical ingredients dissolved or dispersed therein. It also relates to a process for the preparation of said core sheath drug delivery devices, and to its use for contraception.

BACKGROUND ART

Various drug eluting devices have been described. Generally, a monolithic device will elute a drug with first order kinetics with a high initial release followed by a continually tapering release. When zero order steady release is desired, a more complex device is required.

Published U.S. Patent Application No. 2010/0034863 discloses the use of encapsulated active pharmaceutical ingredients in a monolithic device to achieve zero order release.

EP Patent 1,732,520 B1 discloses the use of a core sheath device with both the core and sheath being made of ethylene vinyl acetate. One disadvantage of using ethylene vinyl acetate as the core material is that only hydrophobic drugs are soluble in ethylene vinyl acetate and even then to relatively low degrees. In practice, this results in limiting the amount of drug that can be released on a daily basis from such rings. A further related disadvantage is that ethylene vinyl acetate is essentially non-water swellable, thus it does not allow for the exploitation of water soluble drugs.

SUMMARY OF THE INVENTION

The inventors have developed a device comprising a polyurethane core and a sheath comprising an essentially non water swellable polymer, such as ethylene vinyl acetate, which is easy to prepare and may be designed to provide the release of active ingredients in a substantially constant ratio over a prolonged period of time. The devices of the invention may be used in particular for contraception.

It is well-known that polyurethanes swell in water. This makes it potentially difficult to work with drug eluting devices comprising polyurethane as its physical properties change when exposed to in-vivo conditions. Also, as polyurethanes swell, drugs which have water solubility will elute from the device in an altered way, more quickly the more water soluble the drug is.

The inventors have found that when the polyurethane core is surrounded with a less water swellable polymer than the core, e.g., ethylene vinyl acetate (EVA), the sheath is able to regulate the polyurethane drug release even though the polyurethane still swells.

Thus, it has been found that, even with a sheath comprising a non water swellable polymer, such as an EVA sheath, enough water gets to the polyurethane to swell it, and that the EVA sheath is still able to provide control over the drug release. In particular, as it will be shown in detail in the examples, the release from a device with a polyurethane core and an EVA sheath, wherein the vinyl acetate content is comprised from 15 to 30% w/w, follows essentially zero order kinetics, as desired for in vivo delivery of a highly potent drug. Besides, data in the examples demonstrate that the hydration level of the device, particularly the core, can also be controlled depending on the vinyl acetate content of the EVA used in the sheath.

Moreover, an advantage of the devices of the invention is that the EVA sheath provides structural integrity, in the case where the water swollen polyurethane lacks sufficient structural integrity.

A further advantage of the device of the invention is that, for a drug that is less soluble in water (hydrophobic drugs)— and more soluble in the non-hydrated polyurethane—when the polyurethane hydrates, the effective solubility of the drug will drop providing the situation where there is an excess of drug relative to solubility in the non hydrated polymer. This results in the optimal conditions for sustained zero order release; room temperature stability, preferably when the ring is kept under non-hydrated conditions; and stability in terms of drug solid state because the solubility is maintained.

Therefore, an aspect of the invention relates to a device comprising: (a) a core, said core comprising polyurethane; (b) a sheath, said sheath substantially or completely surrounding said core, said sheath comprising ethylene vinyl acetate copolymer; and (c) one or more active pharmaceutical ingredients dissolved or dispersed in said core and/or said sheath. This aspect can also be formulated as a device comprising: (a) a core comprising polyurethane; (b) a sheath comprising ethylene vinyl acetate copolymer, which substantially or completely surrounds the core; and (c) one or more active pharmaceutical ingredients dissolved or dispersed in the core and/or the sheath.

Another aspect of the invention relates to the use of the device as defined above for contraception.

DETAILED DESCRIPTION OF THE INVENTION

Figure 1:
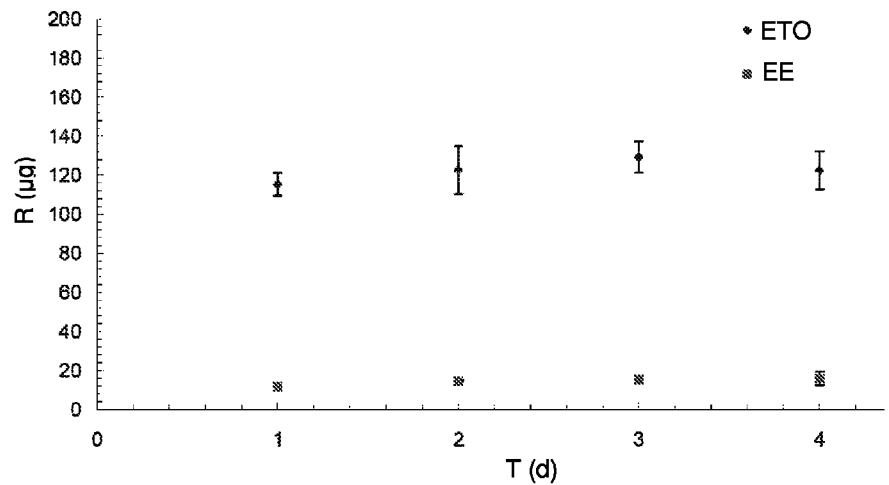
FIG. 1 shows the daily In-vitro Elution (IVE) (release (R) (µg) vs time (T) in days (d)) from the ETO/EE intravaginal ring of example 1 into 0.05% Solutol HS 15 (polyethylenglycol 660—12-hydroxystearate) in 25 mM sodium acetate (pH 4.2).

Provided by the present invention is a core sheath drug delivery device.

For the purposes of the invention, the term "API" means active pharmaceutical ingredient and is used as a synonym of drug.

The term "dissolved", as used herein, means that one or more active pharmaceutical ingredients form a solution in the core polymer or the sheath polymer, so that they are distributed in the core polymer or the sheath polymer forming a homogeneous phase. The solution may be supersaturated, saturated or non-saturated. As used herein, the term "supersaturated" refers to a solution containing a concentration of the active pharmaceutical ingredient that is higher than its saturation concentration at a given temperature, in particular at room temperature, provided that crystallization or precipitation of the active pharmaceutical ingredient does not take place (i.e., the active pharmaceutical ingredient is still completely dissolved). The term "saturated" refers to a solution containing a concentration of the active pharmaceutical ingredient that is equal to the saturation concentration at a given temperature. The term "non-saturated" refers to a solution containing a concentration of the active pharmaceutical ingredient that is lower than the saturation concentration at a given temperature.

The term "dispersed", as used herein, means that one or more active pharmaceutical ingredients form a dispersion in the core polymer or sheath polymer, so that they form aggregates or powders that are suspended in and surrounded by a continuous phase.

For the purposes of the invention, room temperature is 20-25° C.

The term "water-swellable" is used herein to refer to a polymer that in the presence of water is capable of swelling (i.e., expanding, by absorbing water) by at least 5% of its original mass at room temperature and atmospheric pressure.

The term "saturation concentration" ($C_{sat}$) of an active pharmaceutical ingredient in polyurethane refers to the maximum amount of the active ingredient, in particular a progestin, that can be dissolved in the polyurethane polymer at a given temperature, in particular at room temperature. The saturation concentration of the active ingredient in the polyurethane can be determined by several methods well-known in the art.

For instance, a first method for determining the saturation concentration can be performed by exposing the core polymer to a continuous source of active ingredient until the core polymer is saturated as measured through serial assays.

On the one hand, this can be performed by visual observation of various API/polyurethane matrix formulations containing increasing concentrations of APIs as shown in the examples. If the formulations after melt mixing are observed to be transparent, this indicates that the API is soluble in the polyurethane up to the tested concentration, the saturation concentration has not been reached, and the API concentration is below $C_{sat}$. On the contrary, if the formulations after melt mixing and storage appear opaque, showing evidence of undissolved API crystals in the polymer matrix, this indicates that the saturation concentration has been reached, and the API concentration is above $C_{sat}$.

On the other hand, the first method can be performed by measuring the average release (μg/day) of the API for various API/polyurethane matrix formulations containing increasing concentrations of APIs. This is based on the fact that when drug, in the core of a core-sheath system, is present in a dissolved state, the concentration of API will gradually decrease in time and, as a consequence, the release rate will also decrease. If the release rate for a given API concentration increases with respect to a formulation containing a lower API concentration, this indicates that the API concentration is below $C_{sat}$. If the release rate for a given API concentration does not increase with respect to a formulation containing a lower API concentration, this means that the API concentration is above $C_{sat}$. Under these conditions increasing the API concentration does not have any effect on the release rate, since the amount of dissolved drug is fixed by its saturation solubility.

A further method for determining the saturation concentration, if suitable as determined by polymer physicochemical properties, comprises saturating a flat film of the polyurethane with saturated aqueous solution of API and analyzing the film after a predetermined soak duration. It is expected that the polyurethane will absorb the solution and swell, which in turn might influence the saturation concentration determined. As an example, this method comprises the following steps: a) Preparing placebo Hydrothane films 5 cm×5 cm×200 μm thick; b) Immersing in saturated aqueous solution of API at 25° C., c) Incubating for 6 weeks to ensure maximum saturation is achieved, indicated by no significant difference between earlier samples and final sample, and d) Assaying for content.

Alternatively, the latter method, if suitable as determined by polymer physicochemical properties, can be performed using non-aqueous solvents. In such case, the method comprises saturating a flat film of the polyurethane with saturated non-aqueous solution of API and analyzing the film after a predetermined soak duration. The non-aqueous solvent is expected to limit the swelling of the polyurethane and hence should produce a better representation of the determined saturation concentration. Suitable solvents for this method are acetonitrile or acetone.

Finally, a further method for determining the saturation concentration, if suitable as determined by polymer physicochemical properties, comprises sandwiching a separating membrane between an API loaded and an API deficient polyurethane film. The API loaded film will contain excess API, in both dissolved and dispersed state. The API partitions from the API rich film to the API deficient film until the deficient film reaches a state of equilibrium, where no more dissolved API can migrate into its matrix. This is determined to be its point of saturation i.e. $C_{sat}$. As an example, this method comprises the following steps: a) Preparing API loaded Hydrothane films (20% loaded by wt.) 5 cm×5 cm×200 μm thick, b) Preparing placebo Hydrothane films 5 cm×5 cm×200 μm thick, c) Preparing thinner film of separating membrane (EVA-9) 5 cm×5 cm×100 μm, d) Sandwiching a separating membrane between API loaded and placebo Hydrothane films, e) Incubating, f) Removing at predetermined time points (2-12 wks), and g) Assaying 'placebo' film for content.

The device of the present invention is suitable for drug delivery. Thus, in one embodiment, the invention relates to a drug delivery system or a drug eluting device that enables the introduction of a therapeutic substance into the body at the local or systemic level and improves its efficacy and safety by controlling the rate, time and place of release of the drug in the body.

The core of the device comprises polyurethane. Polyurethane (PU) is a polymer composed of a chain of organic units joined by carbamate (urethane) links. Examples of suitable polyurethanes, which can be used as core polymers include, without limitation, aliphatic polyether-based thermoplastic polyurethanes, aliphatic hydrophilic polyether-based thermoplastic polyurethanes, aromatic polyether-based thermoplastic polyurethanes, aliphatic polycarbonate-based thermoplastic polyurethanes, aromatic polycarbonate-based thermoplastic polyurethanes, aromatic polyether based polyurethane elastomers, thermoplastic polyether poly(urethanes), thermoplastic silicone polyether polyurethanes, thermoplastic silicone polycarbonate polyurethanes and hydrophilic thermoplastic polyurethane elastomers. Commercially available suitable polyurethanes include, without limitation, Tecophilic®, Tecoflex®, Tecothane®, Carbothane®, Chronothane®, Elasthane®, Pursil®, and Hydrothane®.

In a preferred embodiment, optionally in combination with one or more features of the various embodiments described above or below, the polyurethane is a hydrophilic aliphatic polyurethane or an aromatic polyurethane. More preferably, a hydrophilic aliphatic polyurethane ranging in water absorption from 5 to 40% by weight, more preferably from 10 to 25% by weight.

In a preferred embodiment, the polyurethane is a hydrophilic aliphatic polyurethane having shore hardness of 50 to 95 A as measured by durometer test. More preferably, the polyurethane have a shore hardness of 75 A. The hardness value measured by durometer test is determined by the penetration of the Durometer indenter foot into the sample. The Shore A scale is used for 'softer' rubbers while the Shore D scale is used for 'harder' ones.

In a preferred embodiment, the polyurethane is a hydrophilic aliphatic polyurethane having a melting point ranging from 70-220° C. More preferably, the polyurethane has a melting point ranging from 100-140° C. The melting point is measured by Differential Scanning calorimetry, or DSC, which is a thermal analysis technique that looks at how a material's heat capacity (Cp) is changed by temperature. A sample of known mass is heated or cooled and the changes in its heat capacity are tracked as changes in the heat flow.

In one embodiment, the core polymer comprises at least 50% polyurethane. In one embodiment, the core comprises at least 60% polyurethane. In one embodiment, the core comprises at least 70% polyurethane. In one embodiment, the core comprises at least 80% polyurethane. In one embodiment, the core comprises at least 90% polyurethane. In one embodiment, the core comprises at least 95% polyurethane. In one embodiment, the core consists essentially of polyurethane, i.e., the core comprises from 50 to 100%, more particularly 75 to 100% of polyurethane.

The above percentages refer to weight percentages (polyurethane weight in respect to core weight).

The core may further comprise one or more of the following additives: release-modifying substances including, without limitation, polyethylene glycerol, glucose, glycine, ascorbic acid, hydroxyethylcellulose, croscarmellose, lactose; fillers including, without limitation, high surface area fumed and precipitated silicas, clays such as kaolin, crushed quartz, diatomaceous earths, calcium carbonate, barium sulphate, iron oxide, titanium dioxide and carbon black; antioxidants including, without limitation, octadecyl-3-(3,5-di-tert.butyl-4-hydroxyphenyl)-propionate (Irganox®), ethylenediaminetetraacetic acid (EDTA), butylated hydroxytoluene (BHT), citric acid (CA), butylated hydroxyanisole (BHA), tertiary butylhydroquinone (TBHQ), and propyl 30 gallate (PG) and alpha-tocopherol; lubricants including, without limitation, irgawax, talc, aerosil and stearates such as magnesium stearate; and excipients including, without limitation, water-soluble or water-swellable polysaccharides, such as croscarmellose (cross linked carboxymethyl cellulose) or hydroxyethylcellulose, glucose, lactose or other mono- or di-saccharides, or their water-soluble salts, proteins such as gelatin, nonionic surface active agents, bile salts, organic solvents, such as ethoxydiglycol, polyethylene glycol and fatty acid esters.

The core may further comprise one or more active pharmaceutical ingredients dissolved or dispersed therein. In one embodiment, the one or more active pharmaceutical ingredients are present at less than their saturation concentration in the polyurethane.

In a preferred embodiment, the active pharmaceutical ingredients are present in the core, so that the sheath does not initially contain any active ingredients. Thus, in a particular embodiment, the invention relates to a device comprising: (a) a core comprising polyurethane; (b) a sheath comprising ethylene vinyl acetate copolymer, which substantially or completely surrounds the core; and (c) one or more active pharmaceutical ingredients dissolved or dispersed in the core. In a more preferred embodiment, the active pharmaceutical ingredients are dissolved in the core.

As used herein, the expression a sheath "substantially surrounding the core" means that at least 90% of the core surface area, more particularly 95%, more particularly 100%, is surrounded by the sheath. In a preferred embodiment, the sheath of ethylene vinyl acetate copolymer completely surrounds the core.

Examples of active pharmaceutical ingredients which can be delivered via the devices of the present invention include, but are not limited to, antibacterial agents, antiviral agents, antifungal agents, chemotherapeutics, hormones, prohormones (e.g. dehydroepiandrosterone (DHEA)), anesthetics, analgesics, antibodies, antigens, muscle stimulants, psychoactive compounds, anti-cholinergic agents (e.g. oxybutynine) and other drugs for contraception, to improve fertility, pregnancy, endometriosis, vaginal atrophy, sexual dysfunction in post-menopausal women, overactive bladder syndrome and urge urinary incontinence and combinations thereof.

In a preferred embodiment, optionally in combination with one or more features of the various embodiments described above or below, the device, preferably the core, comprises a progestin, more preferably a steroidal progestin.

Examples of progestins, also referred to as progestogens or progestogenic compounds, include, without limitation, desogestrel, etonogestrel (3-keto desogestrel), levonorgestrel, norgestrel, gestodene, drospirenone or any other compound with progestogenic activity. i.e, a compound that resembles an effect caused by progesterone.

More preferably, the progestin is selected from etonogestrel and levonorgestrel.

The inventors have found that progestins are very soluble in the core polymer, in particular at the below mentioned concentrations. Thus, progestins are present in a concentration which is lower than its saturation concentration, and hence there is no tendency for the progestin to crystallize over time, at any practical temperature. As a consequence, the devices of the invention are stable when stored at room temperature over prolonged periods of time, in particular over at least 6 months. This has the advantage that the devices do not require expensive storage and transport below room temperature.

In a more preferred embodiment, the progestin is present in the core in a concentration which is lower than its saturation concentration at 25° C.

In an even more preferred embodiment, the progestin is etonogestrel and is present in a concentration which is lower than its saturation concentration at 25° C. comprised from 0.20 to 1.00 wt % based on the total core weight.

In another more preferred embodiment, the progestin is levonorgestrel and is present in a concentration which is lower than its saturation concentration at 25° C. comprised from 0.20 to 1.00 wt % based on the total core weight.

In another preferred embodiment, optionally in combination with one or more features of the various embodiments described above or below, the device, preferably the core, comprises an estrogen, more preferably a steroid estrogen.

Examples of estrogens, also referred to as estrogenic compounds, include, without limitation, estradiol, estriol, mestranol, estradiol-valerate and ethinyl estradiol.

In a more preferred embodiment, the estrogen is ethinyl estradiol. More preferably, ethinyl estradiol is present, preferably in the core, in a concentration comprised from 0.10 to 0.30 wt % based on the total core weight.

In a preferred embodiment, optionally in combination with one or more features of the various embodiments described above or below, the device, preferably the core, comprises a progestin, such as etonogestrel or levonorgestrel, and an estrogen, such as ethinyl estradiol. In a more preferred embodiment, the device, preferably the core, comprises etonogestrel and ethinyl estradiol.

In a more preferred embodiment, the weight ratio of progestin and estrogen is comprised from 10.0 to 1.0, more particularly from 5.0 to 2.0.

As mentioned above, the sheath of the device comprises ethylene vinyl acetate (EVA) copolymer. EVA is a semi-crystalline copolymer of ethylene and vinyl acetate (VA) monomers. The specific ethylene vinyl acetate copolymer of the sheath to be used will depend on the desired drug flux and can be any commercially available ethylene vinyl acetate copolymer. In one embodiment, optionally in combination with one or more features of the various embodiments described above or below, the sheath comprises an EVA copolymer having a vinyl acetate (VA) content comprised from 1 to 50% w/w, more particularly from 10 to 40% w/w, and even more particularly 15 to 30% w/w. In a preferred embodiment, the EVA sheath copolymer has a vinyl acetate content of about 28% w/w. In another preferred embodiment, the EVA sheath copolymer has a vinyl acetate content of about 18% w/w.

For the purposes of the invention, the "vinyl acetate content" refers to the vinyl acetate content in weight based on the total weight of the ethylene vinyl acetate copolymer.

The vinyl acetate content in the EVA sheath controls the rate and degree of hydration of the polyurethane core. As demonstrated in the examples, lower vinyl acetate VA content will allow for less swelling.

Suitable commercially available ethylene vinyl acetate copolymers include the products available under the trade names: Elvax®, VitalDose®, Evatane®, Lupolen V®, Movriton®, Ultrathene®, Ateva®, Vestypar®, Dupont 760, Equistar UE637-000, Huntsman PE1903, and F100309 (Exxon Mobil).

In one embodiment, the sheath comprises at least 50% ethylene vinyl acetate. In one embodiment, the sheath comprises at least 60% ethylene vinyl acetate. In one embodiment, the sheath comprises at least 70% ethylene vinyl acetate. In one embodiment, the sheath comprises at least 80% ethylene vinyl acetate. In one embodiment, the sheath comprises at least 90% ethylene vinyl acetate. In one embodiment, the sheath comprises at least 95% ethylene vinyl acetate. In one embodiment, the sheath consists essentially of ethylene vinyl acetate, i.e., the sheath comprises from 50 to 100%, more particularly from 75 to 100% of ethylene vinyl acetate.

The above percentages refer to weight percentages (ethylene vinyl acetate weight in respect to sheath weight).

The sheath may further comprise one or more of the following additives: a release-modifying substances including, without limitation, polyethylene glycerol, glucose, glycine, ascorbic acid, hydroxyethylcellulose, croscarmellose, lactose; fillers including, without limitation, high surface area fumed and precipitated silicas, clays such as kaolin, crushed quartz, diatomaceous earths, calcium carbonate, barium sulphate, iron oxide, titanium dioxide and carbon black; antioxidants including, without limitation, octadecyl-3-(3,5-di-tert.butyl-4-hydroxyphenyl)-propionate (Irganox®), ethylenediaminetetraacetic acid (EDTA), butylated hydroxytoluene (BHT), citric acid (CA), butylated hydroxyanisole (BHA), tertiary butylhydroquinone (TBHQ), propyl 30 gallate (PG) and alpha-tocopherol; lubricants including, without limitation, irgawax, talc, aerosil and stearates such as magnesium stearate; and excipients including, without limitation, water-soluble or water-swellable polysaccharides, such as croscarmellose (cross linked carboxymethyl cellulose) or hydroxyethylcellulose, glucose, lactose or other mono- or di-saccharides, or their water-soluble salts, proteins such as gelatin, nonionic surface active agents, bile salts, organic solvents, such as ethoxydiglycol, polyethylene glycol and fatty acid esters.

In a particular embodiment, optionally in combination with one or more features of the various embodiments described above or below, the core weight represents from 70 to 95 wt % of the total device weight, and the sheath weight represents from 5 to 30 wt % of the total device weight, being the total device weight 100%.

In a preferred embodiment, optionally in combination with one or more features of the various embodiments described above or below, the device sheath has a thickness comprised from 5 to 500 µm, more particularly from 25 to 250 µm, more particularly from 50 to 200 µm.

Figure 5:
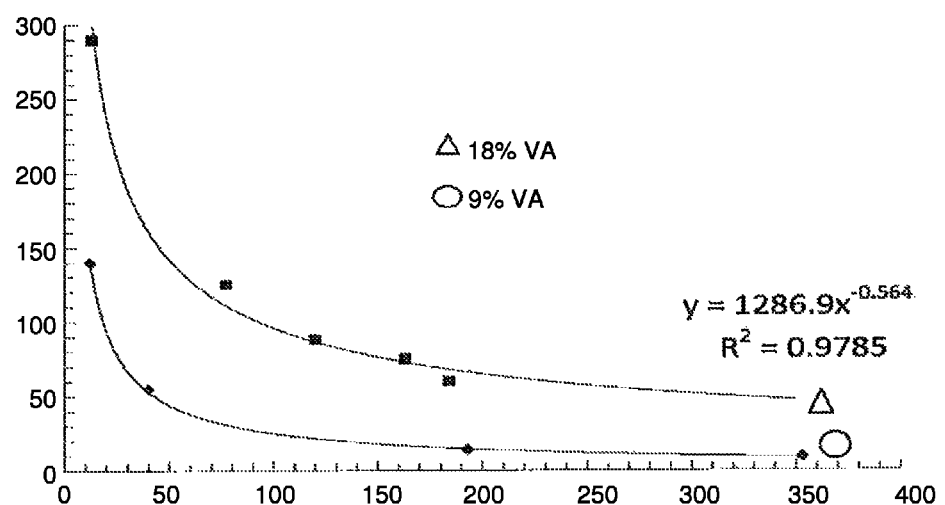
FIG. 5 shows the mean daily In-vitro Elution (IVE) (mean release (µg/day)) vs the sheath thickness (µm) for the LNG intravaginal ring of examples 13-16 having VA content of 18% w/w and of examples 17-20 having VA content of 9% w/w.

An advantage of the devices of the invention is the control over the EVA sheath thickness. When the device of the invention is manufactured the polyurethane is "non-hydrated" and has a certain volume. The sheath substantially or completely surrounds this volume such that a given weight of EVA will have a given thickness. Indeed, during manufacture the sheath thickness is tightly controlled. For a given EVA, it is the sheath thickness that controls the drug release rate. As the polyurethane swells in vivo, it expands. Since the sheath is an elastomer, this core expansion stretches the sheath which decreases its thickness. Generally, a thinner sheath will release more drug, this being one way to lower the burst of drug. Reference is made to FIG. 5.

A further advantage of the devices of the invention is the control over the VA content of EVA sheath. For a given sheath thickness, it is the VA content of EVA that controls the drug release rate. Generally, a lower VA content will release less drug. Reference is made to FIG. 5.

The sheath may further comprise one or more active pharmaceutical ingredients dissolved or dispersed therein.

Examples of active pharmaceutical ingredients which can be delivered via the devices of the present invention include, but are not limited to antibacterial agents, antiviral agents, antifungal agents, chemotherapeutics, hormones, prohormones (e.g. dehydroepiandrosterone (DHEA)), anesthetics, analgesics, antibodies, antigens, muscle stimulants, psychoactive compounds, anti-cholinergic agents (e.g. oxybutynine) and other drugs for contraception, to improve fertility, pregnancy, endometriosis, vaginal atrophy, sexual dysfunction in post-menopausal women, overactive bladder syndrome and urge urinary incontinence and combinations thereof.

In one embodiment, optionally in combination with one or more features of the various embodiments described above or below, the one or more active pharmaceutical ingredients are encapsulated prior to incorporation into the device.

For the purposes of the invention, the term "encapsulated" means that the active pharmaceutical ingredient is dissolved or dispersed in an encapsulation material.

Examples of encapsulation materials include, without limitation, natural or synthetic waxes or wax-like materials such as beeswax, carnauba wax, hydrogenated vegetable oils, stearyl alcohol, and cetyl alcohol, polymeric materials such as polyurethane, polyethylene, polyethylene glycol, polyvinyl alcohol, and silicone polymers, naturally occurring gelling agents such as gelatin, gellan gum, carregenens, and alginates, and combinations thereof. Generally, the active pharmaceutical ingredients can be encapsulated by several processes well-known in the art, including, without limitation, melt-chill processes, solvent emulsification processes, and spray-drying.

The device of the invention may be used in contraception. In particular, the device of the invention may release the progestin in adequate amounts and rates for the above mentioned use. In a more particular embodiment, optionally in combination with one or more features of the various embodiments described above or below, the core comprises etonogestrel and ethinyl estradiol in concentrations that allow an average release rate of 90-150 μg, preferably 120 μg, etonogestrel, and 5-30 μg, preferably 15 μg ethinyl estradiol per 24 hours in situ, over a period of at least 21 to 28 days, preferably 21 days or 24 days or 28 days.

In a more particular embodiment, optionally in combination with one or more features of the various embodiments described above or below, the core comprises levonorgestrel in concentrations that allow an average release rate of 50 to 200 μg, preferably 100 to 150 μg, levonorgestrel per 24 hours in situ, over a period of at least 24 to 28 days, preferably 24 days.

In a preferred embodiment, the device of the invention comprises (a) a core of polyurethane, (b) a sheath of ethylene vinyl acetate having a vinyl acetate content comprised from 10 to 40%, preferably from 15 to 30%, which completely surrounds the core, and (c) etonogestrel and ethinyl estradiol dissolved in the core; wherein etonogestrel is present in a concentration which is lower than its saturation concentration at 25° C. and is comprised from 0.20 to 1.00 wt % based on the total core weight; ethinyl estradiol is present in a concentration comprised from 0.10 to 0.30 wt % based on the total core weight; and the sheath has a thickness comprised from 50 to 200 μm.

In a preferred embodiment, optionally in combination with one or more features of the various embodiments described above or below, the device of the invention comprises (a) a core of polyurethane, (b) a sheath of ethylene vinyl acetate having a vinyl acetate content comprised from 10 to 40%, preferably from 15 to 30%, which completely surrounds the core, and (c) levonorgestrel dissolved in the core; wherein levonorgestrel is present in the core in a concentration which is lower than its saturation concentration at 25° C. and is comprised from 0.20 to 1.00 wt % based on the total core weight; and the sheath has a thickness comprised from 50 to 200 μm.

The inventors have found that, when the devices of the invention, in particular the above mentioned devices, are subjected to tissue or in-vitro release media, the one or more active pharmaceutical ingredients are eluted at or near zero order, thus minimizing potential peak/trough fluctuations and side effects, while maximizing the amount of time the drug concentrations remain within the therapeutic window (efficacy). By zero or near zero order is meant herein that a substantially constant amount or a constant amount of drug per unit time is released over a given period of time. For the purposes of the invention, the term "substantially constant amount" is as defined by the Higuchi formula, see Journal Pharmaceutical Sciences 1963, vol. 52, 1145-1149.

Additionally, the above mentioned devices also show low initial burst release. The term "burst release" refers to a rate of release over time of an active pharmaceutical ingredient wherein the rate is not uniform, but is generally greater during a given period of time, typically immediately following emplacement of the device bearing active pharmaceutical ingredient in tissue.

The drug delivery device of the present invention can have several shapes, such a spiral shape, a T-shape or a ring shape. In a particular embodiment, optionally in combination with one or more features of the various embodiments described above or below, the drug delivery device of the invention is ring-shaped. More particularly, the ring-shaped device has an outer diameter comprised from 50 to 60 mm, more particularly from 52 to 56 mm, and an inner from 40 to 48 mm, more particularly from 44 to 48 mm and has a cross sectional diameter comprised from 2.5 to 8 mm, preferably of 4 mm.

In another particular embodiment, optionally in combination with one or more features of the various embodiments described above or below, the device of the invention is a cylindrical fibre, comprising a cylindrical core and a cylindrical sheath surrounding the core. More particularly, the cylindrical fibre has a cross sectional diameter comprised from 2.5 to 8 mm, preferably of 4 mm.

The drug delivery device of the invention may be used for the intravaginal administration of one or more active ingredients. Thus, in a particular embodiment, optionally in combination with one or more features of the various embodiments described above or below, the device is a vaginal ring. In a more particular embodiment, the device (vaginal ring) comprises progestin and/or an estrogen loaded into the core of the device.

As will be understood by the skilled artisan upon reading this disclosure, however, alternative forms for a device including, but not limited to, rods, spheres and other shapes as dictated by the specific application are encompassed by the present invention. A wafer, for example, may provide a suitable shape for an ocular implant.

In another particular embodiment, optionally in combination with one or more features of the various embodiments described above or below, the device of the invention comprises only one compartment, which comprises the polyurethane core, the EVA sheath, and one or more active pharmaceutical ingredients as defined above. In another embodiment, the device of the invention further comprises another additional compartment, which is a placebo (non-medicated) compartment or a compartment loaded with one or more other active ingredients.

The ring-shaped device of the invention may be prepared by any suitable process. In one embodiment, the process for the preparation of the ring-shaped device comprises a) co-extruding the drug-loaded core and the non-medicated outer sheath, b) cutting the resulting fibres into pieces of the required length, and c) assembling each piece to a ring shaped device.

In another particular embodiment, optionally in combination with one or more features of the various embodiments described above or below, the invention relates to a process for the preparation of the device as defined above, which comprises the following steps:

(i) providing a drug-loaded homogenous polyurethane core granulate, comprising one or more active pharmaceutical ingredients dissolved or dispersed therein, more particularly, dissolved therein, (ii) co-extruding the core granulate with a ethylene vinyl acetate copolymer sheath granulate, resulting in a copolymer fiber comprising a core covered by a sheath;

(iii) cutting the resulting fibres into pieces of the required length, and (iv) assembling the fibre into a ring.

More particularly, step (i) of the above process comprises providing a drug-loaded homogenous polyurethane core granulate, comprising a progestin, such as levonorgestrel, dissolved therein. Alternatively, step (i) of the above process comprises providing a medicated homogenous polyurethane core granulate, comprising a progestin, such as etonogestrel, and an estrogen, such as ethinyl estradiol, wherein both active ingredients are dissolved in the polyurethane.

In another particular embodiment, optionally in combination with one or more features of the various embodiments described above or below, step (i) of the above process comprises (i1) mixing the active pharmaceutical ingredients, in case more than one active ingredient is present, (i2) mixing the blend obtained in step (i1) with polyurethane, (i3) extruding the blend obtained in step (i2), and (i4) pelletizing the extrudate obtained in step (i3).

In another embodiment, optionally in combination with one or more features of the various embodiments described above or below, in step (iii) the fibres are cut into pieces with a length comprised from 13.5 to 18.5 cm, more particularly, from 15.5 to 15.9 cm, preferably of 15.7 cm.

In another embodiment, optionally in combination with one or more features of the various embodiments described above or below, step iv) comprises joining the cut coaxial fibres of step (iii) into rings by bonding with an adhesive, such as cyanoacrylate or an epoxy based adhesive (gluing). Alternatively, step (iv) comprises joining the cut coaxial fibres of step (iii) into rings by thermally bonding the ends (welding) and/or thermally bonding the ends with an inert polymer.

In another particular embodiment, optionally in combination with one or more features of the various embodiments described above or below, one or more additives as already described above may be added to the drug-loaded homogenous polyurethane core and/or to the non-medicated outer sheath by providing a mixture of the additives with the active ingredients and/or with the polymer of the core and/or the polymer of the sheath by any suitable method well known in the art.

In another embodiment, optionally in combination with one or more features of the various embodiments described above or below, a curing phase may be carried out in order to allow the particles of the active ingredients to migrate to the outer surface, which can occur on coaxial polymer strands alone or after the coaxial polymer strands are bonded to get the ring. This process may occur during storage of the product, but it can be optimized to reduce the time by curing the rings at certain conditions, by controlling temperature and relative humidity. Particularly these conditions may range from 1 day to 4 weeks, preferably 2 weeks, at temperatures from 5° C. to 60° C., preferably at 40° C. and relative humidity from 10% to 80%, preferably 30%.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred implementations described herein.

EXAMPLES

Example 1—Polyurethane/EVA Core-Sheath Intravaginal Ring (IVR) Containing Dual APIs (Etonogestrel and Ethinyl Estradiol)

Due to the photosensitivity of Ethinyl Estradiol (EE), all blending and hot melt extrusions were performed under yellow light, and materials were stored in amber zip-top bags.

Drying of the thermoplastic polyurethane elastomer, Hydrothane AL 25-80A, was required before each thermal processing step. The Hydrothane was dried for 12 hours in a Dri-Air NAFM nitrogen dryer according to the manufacturer's guidelines; with the inflow gas temperature set at 140° F. (60° C.), and gas pressure at ~80 psi (551.58 KPa).

A GlenMills T2F turbula mixer was used to homogenously blend the micronized APIs, Etonogestrel (ETO) and EE by placing 0.68% (by weight of final core batch size) ETO and 0.25% (by weight of final core batch size) EE in a 1000 mL PTFE jar, fitting the jar into the turbula mixer, and blended for 30 minutes at 46 rpm. This active pharmaceutical ingredients (API) blend was then turbula mixed with Hydrothane resin at a 1:1 mass ratio for 30 minutes at 46 rpm. The Hydrothane/API blend was then geometrically diluted in a clear plastic bag with fresh Hydrothane pellets at 1:1 mass ratios by shaking the bag manually by hand for approximately one minute after each addition of fresh Hydrothane, until the target core material batch size of 7 kg was achieved.

A Leistritz ZSE18 twin screw extruder was used to compound the APIs into Hydrothane. The dry blended ETO, EE and Hydrothane were gravity fed into the extruder by hand-feeding the blend through a hopper and extruded out through a two strand die of 2 mm orifice diameter with the extruder process zones set at 200° C. and screw speed set at 100 rpm. The extruded strands were conveyed using a QC Industries conveyer belt fitted with air knives to promote cooling to ambient temperature. The extruded strands were collected and stored in plastic containers with lids. The strands were pelletized by feeding into a Scheer Bay BT-25 pelletizer fitted with a 6 tooth cutter. The pelletized compound was mixed in a Patterson-Kelley Blend Master Lab blender fitted with a 16 qt v-shell for 60 min to homogenize and then dried as a single mass according to the drying section detailed above. The mixed pellets were immediately re-fed into the Leistritz, re-extruded and pelletized as described above to yield homogenously loaded pellets.

The pelletized API loaded Hydrothane was further extruded as the core material through a coaxial extrusion set up consisting of a fixed center bi-component rod crosshead die connected to the exit zones of two single screw extruders fitted at right angles to each other. A Randcastle 1 inch (2.54 cm) 36:1 L/D micro-extruder, model # RCP-1000, was used to feed the core material. A ½ inch (1.27 cm) 24:1 L/D Randcastle micro-extruder, model # RCP-0500, was used to feed the ethylene-vinyl acetate co-polymer (VA content 28% w/w) as sheath material. The core material was dried, as previously described in the drying section and flood fed into the core extruder with process heat zones set at 185° C. and screw speed set at 22 rpm, extruding at an output rate of 1360 g/h. The sheath material was flood fed into the sheath extruder with process heat zones set at 185° C. and screw speed set at 31 rpm, extruding at an output rate of approx. 147 g/h. Both polymers were extruded into the die forming the core-sheath fiber which was water-cooled by passing through a 36-inch (91.44 cm) long water trough containing ambient temperature water and spooled using a Randcastle traversing winder, drawing #001-284, whose tension/uptake rate of 6 ft/min (1.83 m/min) was used to control the fiber diameter, maintaining it at 4 mm. Alternatively, forced air may be used for cooling. The diameter of the coaxial fiber was monitored by passing the material though a laser micrometer or with routine checks using a thickness gauge, calipers or a micrometer.

The coaxial fiber produced was cut to approx. 15.7 cm segment length and the ends thermally bonded using a PlasticWeld Systems HPS-20 Induction Ring Bonder yielding a core-sheath intravaginal ring with an outside diameter of approx. 54 mm, an inside diameter of approx. 46 mm, a cross sectional diameter of approx. 4 mm, and composed of a Hydrothane core, loaded with ETO and EE, and a 100 micrometer thick EVA sheath (Table 1). Alternatively, the coaxial fibers, cut to the desired length, were joined into rings by bonding with cyanoacrylate or an epoxy based adhesive.

TABLE 1

| Components | Mass (g) | % component weight/ring weight |
|---|---|---|
| Hydrothane | 1.9700 | 89.61 |
| EVA | 0.2100 | 9.55 |
| ETO | 0.0135 | 0.61 |
| EE | 0.0050 | 0.23 |
| Total | 2.1985 | 100 |

FIG. 1 shows the daily In-vitro Elution (IVE) from the above ETO/EE intravaginal ring. The in-vitro release rate of etonogestrel and EE for example 1 was determined by immersing the samples in 100 mL of aqueous solution of 0.05% solutol HS-15 in 25 mM sodium Acetate (pH 4.2) at 37° C. under continuous stirring at 60 rpm. In order to maintain sink conditions the water in the containers was refreshed daily. The ETO and EE concentration was determined daily by HPLC using a Waters XBridge C18 column, 5 µm, 4.6×75 mm at column temperature of 30° C., a mobile phase of acetonitril:water, a flow rate of 1.2 mL/min, and an injection volume of 50 µL. Detection was carried out by UV detection at 210 nm.

Example 2—Polyurethane/EVA Core-Sheath Intravaginal Ring (IVR) Containing a Single API (Levonorgestrel)

Due to the photosensitivity of Levonorgestrel (LNG), all blending and hot melt extrusions were performed under yellow light, and materials were stored in amber zip-top bags.

Drying of the thermoplastic polyurethane elastomer, Hydrothane AL 25-80A, was required before each thermal processing step. The Hydrothane was dried for 12 hours in a Dri-Air NAFM nitrogen dryer according to the manufacturer's guidelines; with the inflow gas temperature set at 140° F. (60° C.), and gas pressure at ~80 psi (551.58 KPa).

A GlenMills T2F turbula mixer was used to homogenously blend the micronized LNG with Hydrothane resin at a 1:1 ratio by placing 0.5% (by weight of final batch size) of LNG and Hydrothane pellets (1:1 mass ratio) in a 1000 mL PTFE jar, fitting the jar into the turbula mixer, and blended for one hour at 46 rpm. The blend was then geometrically diluted in a clear plastic bag with fresh Hydrothane pellets at 1:1 mass ratios by shaking the bag manually by hand for approximately one minute after each addition of fresh Hydrothane, until the target batch size of 5 kg was achieved.

A Leistritz ZSE18 twin screw extruder was used to compound the LNG into Hydrothane. The dry blended LNG and Hydrothane were gravity fed into the extruder by hand-feeding the blend through a hopper and extruded out through a two strand die of 2 mm orifice diameter with the extruder process zones set at 180° C. and screw speed set at 120 rpm. The extruded strands were conveyed using a QC Industries conveyer belt fitted with air knives to promote cooling to ambient temperature. The extruded strands were collected and stored in plastic containers with lids. The strands were pelletized by feeding into a Scheer Bay BT-25 pelletizer fitted with a 6 tooth cutter. The pelletized compound was mixed in a Patterson-Kelley Blend Master Lab blender fitted with a 16 qt v-shell for 60 min to homogenize and then dried as a single mass according to the drying section detailed above. The mixed pellets were immediately re-fed into the Leistritz, re-extruded and pelletized as described above to yield homogenously loaded pellets.

The pelletized LNG loaded Hydrothane was further extruded as the core material through a coaxial extrusion set up consisting of a fixed center bi-component rod crosshead die connected to the exit zones of two single screw extruders fitted at right angles to each other. A Randcastle 1 inch (2.54 cm) 36:1 L/D micro-extruder, model # RCP-1000, was used to feed the core material. A ½ inch (1.27 cm) 24:1 L/D Randcastle micro-extruder, model # RCP-0500, was used to feed the ethylene-vinyl acetate co-polymer (VA content 18% w/w) as sheath material. The core material was dried, as previously described in the drying section and flood fed into the core extruder with process heat zones set at 188° C. and screw speed set at 18 rpm, extruding at an output rate of 2008 g/h. The sheath material was flood fed into the sheath extruder with process heat zones set at 188° C. and screw speed set at 31 rpm, extruding at an output rate of approx. 240 g/h. Both polymers were extruded into the die forming the core-sheath fiber which was water-cooled by passing through a 36-inch (91.44 cm) long water trough containing ambient temperature water and spooled using a Randcastle traversing winder, drawing #001-284, whose tension/uptake rate of 9 ft/min (2.74 m/min) was used to control the fiber diameter, maintaining it at 4 mm. Alternatively, forced air may be used for cooling. The diameter of the coaxial fiber was monitored by passing the material though a laser micrometer or with routine checks using a thickness gauge, calipers or a micrometer.

The coaxial fiber produced was cut to approx. 15.7 cm segment length and the ends thermally bonded using a PlasticWeld Systems HPS-20 Induction Ring Bonder yielding a core-sheath intravaginal ring with an outside diameter of approx. 54 mm, an inside diameter of approx. 46 mm, a cross sectional diameter of approx. 4 mm, and composed of a Hydrothane core loaded with LNG and a 120 micrometer thick EVA sheath (Table 2). Alternatively, the coaxial fibers, cut to the desired length, were joined into rings by bonding with cyanoacrylate or an epoxy based adhesive.

TABLE 2

| Components | Mass (g) | % component weight/ring weight |
|---|---|---|
| Hydrothane | 1.934 | 87.92 |
| EVA | 0.256 | 11.64 |
| LNG | 0.0097 | 0.44 |
| Total | 2.1997 | 100 |

Figure 2:
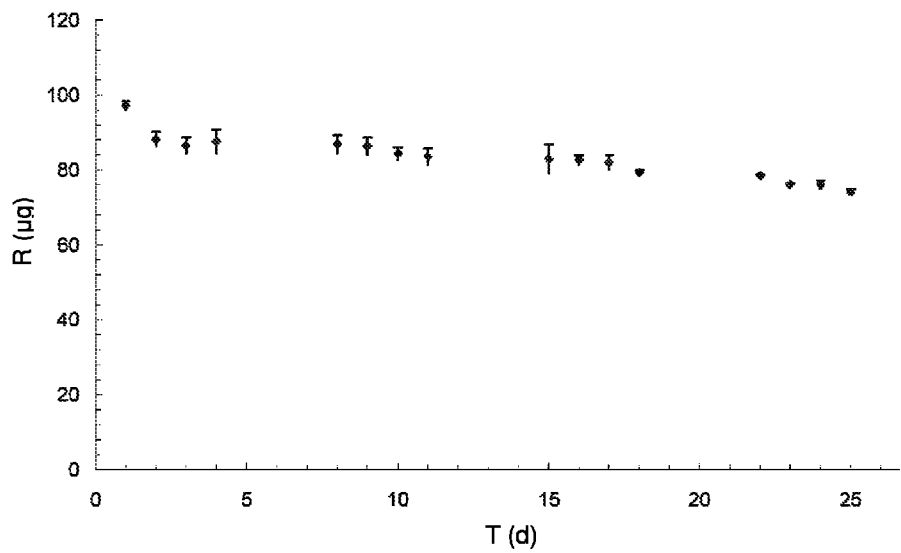
FIG. 2 shows the daily In-vitro Elution (IVE) (release (R) (µg) vs time (T) in days (d)) from the LNG intravaginal ring of example 2 into 0.2 M sodium acetate+1% SLS (Sodium lauryl sulfate) (pH 4.2).

FIG. 2 shows the daily In-vitro Elution (IVE) from the above LNG intravaginal ring. The in-vitro release rate of levonorgestrel for example 2 was determined by immersing the samples in 100 mL of aqueous solution of 1.0% sodium lauryl sulfate (SLS) in 0.2 M sodium Acetate (pH 4.2) at 37° C. under continuous stirring at 60 rpm. In order to maintain sink conditions the water in the containers was refreshed daily. The levonorgestrel concentration was determined daily by HPLC using a Waters XBridge C18 column, 5 µm, 4.6×75 mm at column temperature of 30° C., a mobile phase of acetonitrile:water, a flow rate of 1.2 mL/min, and an injection volume of 25 µL and ambient sample temperature. Detection was carried out by UV detection at 245 nm.

Determination of the Solubility of the Active Pharmaceutical Ingredients in Polyurethane Via Visual Inspection Levonorgestrel (LNG) and Etonogestrel (ETO) solubility in the hydrophilic polyurethane (PU), Hydrothane AL 25-80A, were determined by visual observation of API/PU formulations after melt mixing. The API was compounded into the polyurethane matrix at various concentrations until visual evidence of undissolved API crystals was observed.

a) Preparation of Matrix IVRs

A Rheocord 9000 batch compounder with a Banbury mixing attachment was used to compound the API/s into the intravaginal ring (IVR) matrix polymer. The polyurethane polymer, Hydrothane AL 25-80A, was added to the Banbury mixer and allowed to melt with mixing at a temperature of 175° C., for ten minutes at 30 rpm before the addition of the API powder/s (ETO and EE or LNG). Once the API/s was added, the mixing speed was maintained at 30 rpm and mixing was continued for five minutes. After mixing, the Banbury attachment was disassembled and the molten compound was allowed to cool to ambient temperature. After cooling, the compounds were removed from the mixer and stored in a light-protected zip-top bag at ambient conditions.

An AB Machines AB200 injection molder fitted with an aluminum ring mold (4 mm cross-sectional diameter, 54 mm overall diameter) was used to injection mold IVRs. Ground compound was fed into the AB200 injection chamber and melted at a range of 185-190° C. for 5 minutes, and then injected at approx. 80 psi (551.58 KPa) into the 4 mm/54 mm IVR mold. The rings were removed from the mold, and if necessary, excess polymer from the injection (flash) was removed using a razor blade. Rings were then stored in a light protected zip-top bag at ambient conditions.

Following the process above, the following formulations were obtained:

TABLE 3

| Formulation # | APIs loading (% API weight/ring weight) | | |
|---|---|---|---|
| | ETO | EE | LNG |
| 1 | 0.22% | 0.058% | — |
| 2 | 5% | 1.25% | — |
| 3 | — | — | 0.25% |
| 4 | — | — | 0.6% |
| 5 | — | — | 5% |
| 6 | — | — | 10% |
| 7 | — | — | 20% | b) Visual Appearance of APIs in Hydrothane AL 25-80A after Manufacture

Observations of appearance were recorded immediately after manufacture. In the case of formulations with ETO (formulations 1-2), Hydrothane monolithic IVRs containing up to 5% ETO were observed to be transparent indicating API is soluble in Hydrothane up to this tested level. In the case of formulations with LNG (formulations 3-7), Hydrothane monolithic IVRs containing up to 10% LNG were observed to be transparent. 20% LNG loaded IVRs appeared opaque, clearly showing evidence of undissolved API crystals in the polymer matrix. This observation suggests a LNG $C_{sat}$ between 10-20% in Hydrothane AL 25-80A.

c) Visual Appearance of APIs in Hydrothane AL 25-80A after Storage

To investigate if the point of supersaturation was reached, which would be indicated by crystallization of the drug after aging, rings were stored at room temperature, away from light, for up to 6 months. In the case of formulations with ETO (formulations 1-2), Hydrothane/ETO/EE rings appeared transparent at both ETO/EE loading investigated. In the case of formulations with LNG (formulations 3-7), the Hydrothane/LNG rings appear transparent at 0.25% but opaque at 5, 10 and 20%.

Determination of ETO and EE Solubility in Polyurethane by Measuring the Average Release (µg/day) of the API Etonogestrel (ETO) solubility in the hydrophilic polyurethane, Hydrothane AL 25-80A, was determined by evaluating its in-vitro elution (IVE) from core sheath IVRs containing ETO in the core at various loadings. It is referenced in J. A. H van Laarhoven et al., International Journal of Pharmaceutics vol. 232 (2002), 163-173, that when drug, in the core of a core-sheath system, is present in a dissolved state, the API concentration in the core will gradually decrease in time and as a consequence the release rate will also decrease.

Table 4 lists the core sheath formulations evaluated, with API loading and measured sheath thicknesses. These formulations were prepared in an analogous manner to the one described for example 1. The core polymer was Hydrothane AL 25-80A and the sheath polymer EVA VA content 28% w/w. Table 5 details the average 21 days daily elution of the APIs from the core sheath IVRs.

TABLE 4

| Formulation # | % ETO weight/core weight | % EE weight/core weight | Measured sheath thickness (µm) |
|---|---|---|---|
| Example 3 | 0.50 | 0.125 | 80 |
| Example 4 | 0.75 | 0.188 | 83 |
| Example 5 | 1.00 | 0.250 | 83 |

TABLE 5

| Formulation # | Avg. daily ETO release (μg/day) | Avg. daily EE Release (μg/day) |
|---|---|---|
| Example 3 | 87.8 | 8.5 |
| Example 4 | 148.2 | 12.9 |
| Example 5 | 211.1 | 18.1 |

According to these results, it can be observed that the average daily release for the 0.75% ETO concentration was higher than the average daily release for the 0.50% ETO concentration; and the average daily release for the 1.00% ETO concentration was higher than the average daily release for the 0.75% ETO concentration. Thus, it was concluded that the 1.00% ETO concentration was below the $C_{sat}$. With respect to EE, the same effect was observed, so that it was concluded that the 0.25% EE concentration was below the $C_{sat}$.

Determination of the Effects of Water Uptake on Sheath Thickness

The effects of water uptake on sheath thickness were determined. Following an analogous process as described in Example 1 and using Hydrothane AL 25-80A as core polymer and a sheath of EVA having a vinyl acetate content of 28%, the following rings as described in Table 6 below were obtained.

TABLE 6

| Formulation # | % ETO weight/ core weight | % EE weight/ core weight | Measured sheath thickness (μm) |
|---|---|---|---|
| Example 6 | 0.75 | 0.188 | 83 |
| Example 7 | 5.00 | 1.25 | 137 |

The average weight of the rings after its preparation (average pre weight) was measured. The rings were exposed to water. After that the average weight of the rings (average post weight) was measured. From these values the % mass swell as well as the swell ratio were calculated as shown in table 7.

TABLE 7

| Formulation # | Avg. Pre weight (g) | Avg. Post weight (g) | % mass swell | Swell ratio Pre:Post |
|---|---|---|---|---|
| Example 6 | 2.26 | 2.59 | 15 | 1.15 |
| Example 7 | 2.19 | 2.46 | 12 | 1.12 |

The sheath thickness of the hydrated rings was determined based on the measured weights and applying the following formulas:

Assumptions

The swelling is assumed as isotropic so both r and R increase by the same %, i.e. the cube root of the actual swelling hence h increases, when hydrated, by the cube root of the actual swelling Pre and post hydrated sheath density is constant (volume and mass of sheath does not change)

Core density is constant (% change in mass is proportional to % change in vol)

$Vol_{dry\ ring\ sheath} = Vol_{hydrated\ ring\ sheath}$

Since: $Vol_{sheath} = Vol_{total} - Vol_{core}$

Figure 3:
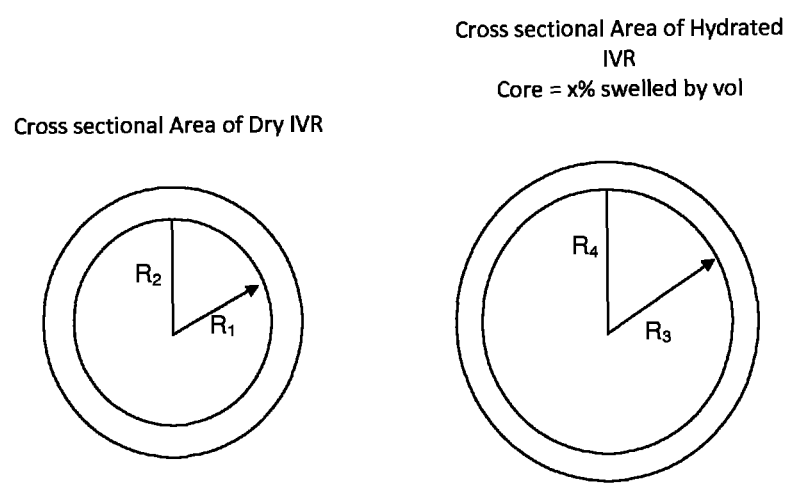
FIG. 3 shows the cross sectional area of dry intravaginal ring (IVR) and the cross sectional area of hydrated IVR.

Then: $(Vol_{total} - Vol_{core})_{dry\ ring\ sheath} = (Vol_{total} - Vol_{core})_{hydrated\ ring\ sheath}$ Taking into account that $R_1$ and $R_2$ are respectively the inner and outer radius of the dry (non-hydrated) ring, and $R_3$ and $R_4$ are respectively the inner and outer radius of the hydrated ring as shown in FIG. 3:

$\rightarrow \pi R_2^2 h_1 - \pi R_1^2 h_1 = \pi R_4^2 h_2 - \pi R_3^2 h_2$ $\rightarrow R_4 = \sqrt{\{(R_2^2 h_1 - R_1^2 h_1 + R_3^2 h_2)/h_2\}}$ And since; $Vol_{hydrated\ core} = $ swell ratio$*V_{dry\ core}$ $\rightarrow \pi R_3^2 h = $ swell ratio$*\pi R_1^2 h$ $\rightarrow R_3 = \sqrt{(\text{swell ratio}*R_1^2)}$ Therefore:

$\rightarrow R_4 = \sqrt{\{(R_2^2 h_1 - R_1^2 h_1 + [\text{swell ratio}*R_1^2 h_2])/h_2\}}$ And since; $h_2 = (\sqrt[3]{\text{swell ratio}})*h_1$ $\rightarrow R_4 = \sqrt{\{(R_2^2 h_1 - R_1^2 h_1 + [\text{swell ratio}*R_1^2*(\sqrt[3]{\text{swell ratio}})*h_1])/(\sqrt[3]{\text{swell ratio}})*h_1\}}$ $\rightarrow R_4 = \sqrt{\{[(R_2^2 - R_1^2)/\sqrt[3]{\text{swell ratio}}] + [\text{swell ratio}*R_1^2]\}}$ (Sheath thickness)$_{dry\ ring} = R_2 - R_1$ (Sheath thickness)$_{hydrated\ ring} = R_4 - R_3$

TABLE 8

| Formulation # | $R_1$ (mm) | $R_2$ (mm) | $R_3$ (mm) | $R_4$ (mm) | (Sheath Thickness)$_{dry}$ (μm) | (Sheath Thickness)$_{hydrated}$ (μm) |
|---|---|---|---|---|---|---|
| Example 6 | 1.917 | 2.000 | 2.056 | 2.130 | 83 | 74 |
| Example 7 | 1.863 | 2.000 | 1.972 | 2.097 | 137 | 125 |

When a PU core/EVA sheath ring is made, the EVA sheath has a certain thickness. As it can be seen in Table 8 the sheath thickness of the hydrated rings is lower than the sheath thickness of the dry rings. This is because as the core swells the EVA sheath is stretched making it thinner.

Determination of the Effects of the VA Content in the Water Uptake on Ring Weight The effects of the VA content in the water uptake on ring weight over time were determined. Following an analogous process as described in Example 1 and using Hydrothane AL 25-80A as core polymer and a sheath of EVA having a vinyl acetate content of 9% w/w or 18% w/w as indicated in the table 9 below, the following rings were obtained.

TABLE 9

| Formulation # | Sheath polymer | Measured sheath thickness (μm) | % of swelling |
|---|---|---|---|
| Example 8 | EVA 9% w/w VA | 50 | 10.2 |
| Example 9 | EVA 9% w/w VA | 100 | 10.1 |
| Example 10 | EVA 18% w/w VA | 50 | 17.6 |
| Example 11 | EVA 18% w/w VA | 100 | 14.2 |
| Example 12 | EVA 18% w/w VA | 200 | 9.4 |

Figure 4:
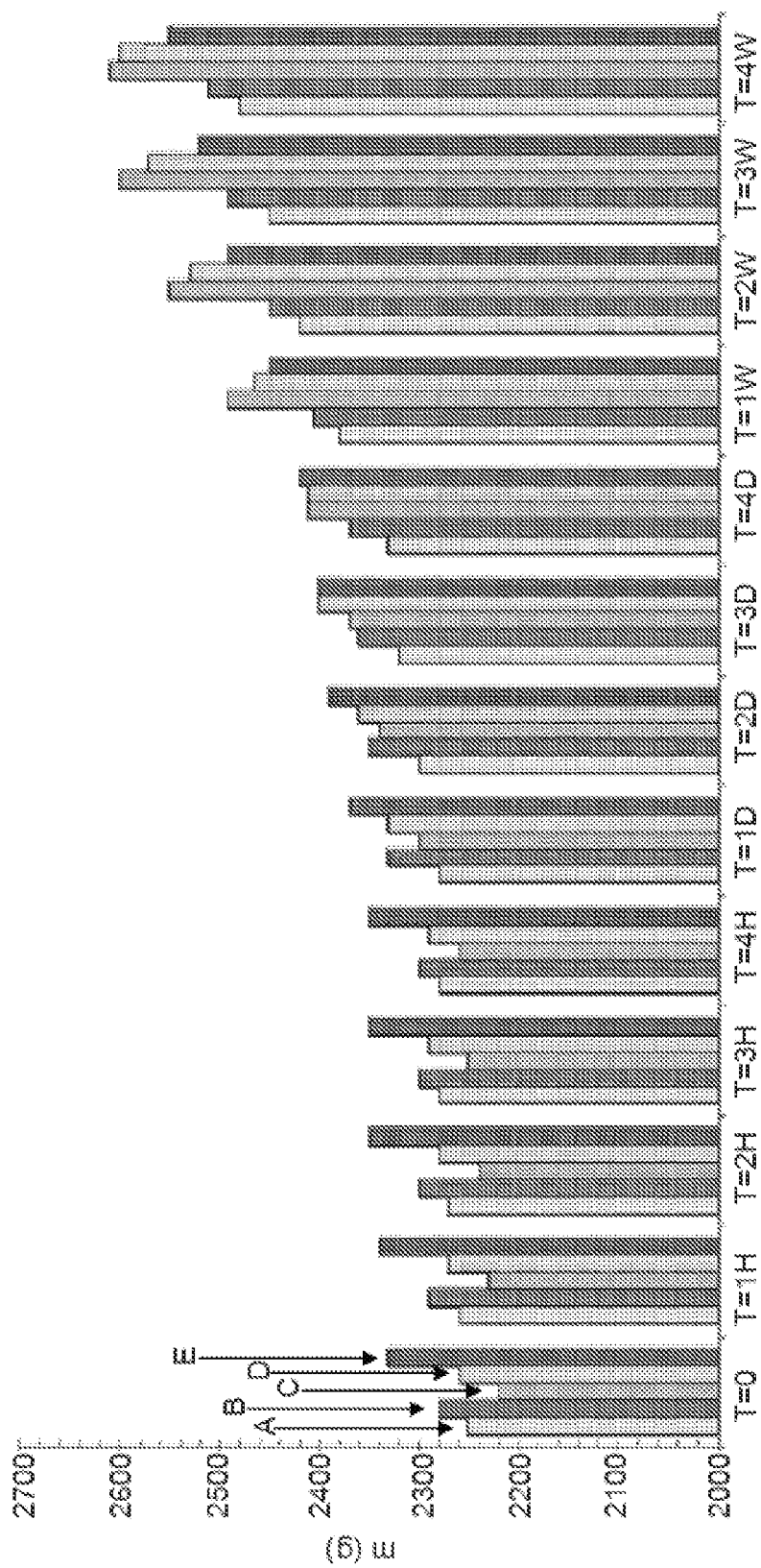
FIG. 4 shows the control of the hydration of the core by the VA content (% w/w) in the EVA sheath over time.

The average weight of each of the rings after its preparation (time point T=0) was measured. The rings were exposed to water. After that the average weight of the rings was measured at different time points (1-4 h, 1-4 days and 1-4 weeks). FIG. 4 shows the average weight (g) of the rings of Examples 8-12 at the different time points. For each given time point the first column (A) of the block corresponds to the ring of Example 8; the second column (B) corresponds to the ring of Example 9; the third column (C) corresponds to the ring of Example 10; the fourth column (D) corresponds to the ring of Example 11; and the fifth column (E) corresponds to the ring of Example 12.

As it can be seen in Table 9 the VA content in the EVA sheath controls the rate and degree of hydration of the core so that the lower VA content will allow for less swelling. Determination of the Effect of Sheath Thickness and VA Content in the EVA Sheath in the Release Rate of the Drug.

For the determination of the effect of the sheath thickness and the VA content in the EVA sheath on the release rate of the drug, the formulations 13-16 were prepared following an analogous process as described in Example 2 and using hydrothane AL 25-28A as core polymer and a sheath of EVA having VA content of 18% w/w and four different sheath thickness. Additionally, formulations 17 to 20 were prepared following an analogous process as described in Example 2 and using hydrothane AL 25-28A as core polymer and a sheath of EVA having VA content of 9% w/w and four different sheath thickness.

The average levonorgestrel release data for each formulation 13-16 having different sheath thickness and % VA content of 18% w/w is shown in table 10 below:

TABLE 10

| Formulation # | Sheath polymer | Measured sheath thickness (μm) | Average Levonorgestrel daily release (μg/day) |
|---|---|---|---|
| Example 13 | EVA 18% w/w VA | 77 | 125 |
| Example 14 | EVA 18% w/w VA | 120 | 85 |
| Example 15 | EVA 18% w/w VA | 163 | 75 |
| Example 16 | EVA 18% w/w VA | 184 | 60 |

The average levonorgestrel release data for each formulation 17-20 having different sheath thickness and VA content of 9% w/w is shown in table 11 below:

TABLE 11

| Formulation # | Sheath polymer | Measured sheath thickness (μm) | Average Levonorgestrel daily release (μg/day) |
|---|---|---|---|
| Example 17 | EVA 9% w/w VA | 12 | 140 |
| Example 18 | EVA 9% w/w VA | 40 | 55 |
| Example 19 | EVA 9% w/w VA | 193 | 14 |
| Example 20 | EVA 9% w/w VA | 353 | 9 |

The average of levonorgestrel daily release was calculated taking into account the daily in vitro daily elution of each formulation during 24 days. The daily in vitro elution was determined using the conditions already disclosed for example 2.

The results of the release rate for the formulation 13-16 of table 10 and formulations 17-20 of table 11 are represented in FIG. 5.

As result it can be concluded that a thinner sheath will release more drug whereas a lower VA content will release less drug.

REFERENCES CITED IN THE APPLICATION

US 2010/0034863
EP 1732520 B1
J. A. H van Laarhoven et al., International Journal of Pharmaceutics vol. 232 (2002), 163-173.
Journal Pharmaceutical Sciences 1963, vol. 52, 1145-1149.

The invention claimed is:

1. A device comprising:
   (a) a core, said core comprising at least 90% of polyurethane,
      wherein the polyurethane is selected from aliphatic polyether-based thermoplastic polyurethanes, aliphatic hydrophilic polyether-based thermoplastic polyurethanes, aromatic polyether-based thermoplastic polyurethanes, aliphatic polycarbonate-based thermoplastic polyurethanes, aromatic polycarbonate-based thermoplastic polyurethanes, aromatic polyether based polyurethane elastomers, thermoplastic polyether poly(urethanes), thermoplastic silicone polyether polyurethanes, thermoplastic silicone polycarbonate polyurethanes and hydrophilic thermoplastic polyurethane elastomers;
   (b) a sheath, said sheath substantially or completely surrounding said core, said sheath comprising from 50 to 100% of ethylene vinyl acetate copolymer,
      wherein the ethylene vinyl acetate copolymer has a vinyl acetate content from 1 to 50% w/w, and,
      wherein said sheath has a thickness from 5 to 500 μm; and
   (c) one or more active pharmaceutical ingredients dissolved or dispersed in said core and/or said sheath;
      wherein the one or more active pharmaceutical ingredients are eluted at or near zero order.

2. The device according to claim 1, wherein the active pharmaceutical ingredients are selected from the group consisting of antibacterial agents, antiviral agents, antifungal agents, chemotherapeutics, hormones, prohormones, anesthetics, analgesics, antibodies, antigens, muscle stimulants, psychoactive compounds, anti-cholinergic agents, and combinations thereof.

3. The device according to claim 1, wherein the active pharmaceutical ingredients are present in the core.

4. The device according to claim 3, wherein the active pharmaceutical ingredients are present in the core in a concentration below its saturation concentration.

5. The device according to claim 1, which comprises an estrogen.

6. The device according to claim 5, wherein the estrogen is ethinyl estradiol.

7. The device according to claim 6, wherein ethinyl estradiol is present in the core in a concentration comprised from 0.10 to 0.30 wt % based on the total core weight.

8. The device according to claim 1, which comprises a progestin.

9. The device according to claim 8, wherein the progestin is etonogestrel.

10. The device according to claim 9, wherein etonogestrel is present in the core in a concentration below its saturation concentration at 25° C. comprised from 0.20 to 1.00 wt % based on the total core weight.

11. The device according to claim 8, wherein the progestin is levonorgestrel.

12. The device according to claim 11, wherein levonorgestrel is present in the core in a concentration below its saturation concentration at 25° C. comprised from 0.20 to 1.00 wt % based on the total core weight.

13. The device according to claim 1, which comprises a progestin and an estrogen.

14. The device according to claim 13, wherein the progestin is etonogestrel and the estrogen is ethinyl estradiol.

15. The device according to claim 14, wherein etonogestrel is present in the core in a concentration below its saturation concentration at 25° C. comprised from 0.20 to 1.00 wt % based on the total core weight; and ethinyl estradiol is present in the core in a concentration comprised from 0.10 to 0.30 wt % based on the total core weight.

16. The device according to claim 1, wherein the ethylene vinyl acetate copolymer has a vinyl acetate content comprised from 10 to 40% w/w.

17. The device according to claim 12, wherein the ethylene vinyl acetate copolymer has a vinyl acetate content comprised from 10 to 40% w/w.

18. The device according to claim 15, wherein the ethylene vinyl acetate copolymer has a vinyl acetate content comprised from 10 to 40% w/w.

19. The device according to claim 1, wherein the sheath has a thickness comprised from 50 to 200 μm.

20. The device according to claim 12, wherein the sheath has a thickness comprised from 50 to 200 μm.

21. The device according to claim 15, wherein the sheath has a thickness comprised from 50 to 200 μm.

22. The device according to claim 1, wherein the device is a vaginal ring.

23. The device according to claim 1, where the pharmaceutical ingredients are encapsulated prior to incorporation into the device.

24. The device according to claim 1, where there is one or more active pharmaceutical ingredients contained in the sheath.

\* \* \* \* \*